Figure 1:
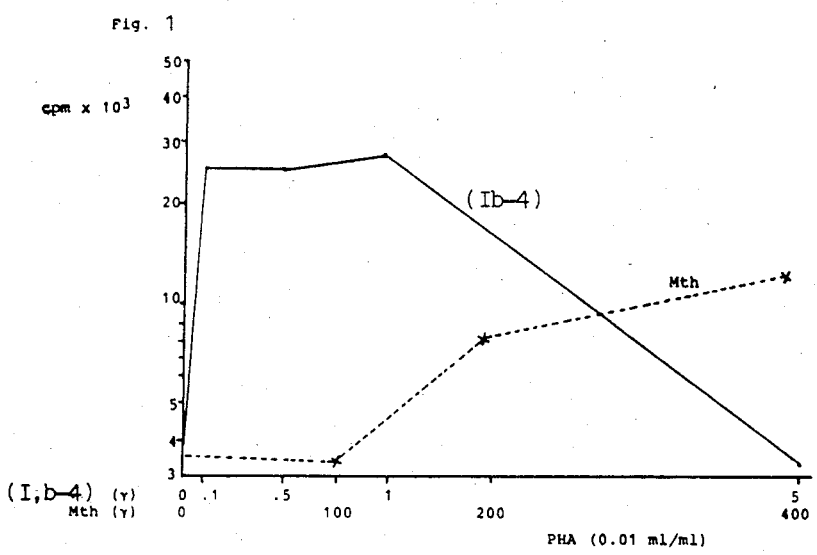

United States Patent [19]

Ferraris

[11] Patent Number: 4,567,182
[45] Date of Patent: Jan. 28, 1986

[54] COMPOUNDS ENDOWED WITH IMMUNOMODULATING ACTIVITY

[75] Inventor: Paolo C. Ferraris, Genoa, Italy

[73] Assignee: Co Pharma Corporation s.r.l., Genoa, Italy

[21] Appl. No.: 418,189

[22] Filed: Sep. 14, 1982

[30] Foreign Application Priority Data

Sep. 24, 1981 [IT] Italy ............................ 24120 A/81
Aug. 13, 1982 [IT] Italy ............................ 22848 A/82

[51] Int. Cl.$^4$ ..................... A61K 31/52; C07D 473/30
[52] U.S. Cl. ................................ 514/262; 544/276; 544/277
[58] Field of Search ............... 544/276, 277; 424/253; 514/262

[56] References Cited

U.S. PATENT DOCUMENTS 4,360,522 11/1982 Schaeffer ........................... 544/276

OTHER PUBLICATIONS

J. W. Hadden, "The Immunopharmacology of Purine-Related Compounds", pp. 131–133.
P. Cornaglia-Ferraris, et al; "L-Aminoacid-Hypoxantine Derivatives Identified as Differentiators of Pre-T Cells in nu/nu Mice".
A. Melodia, et al; "L-Arginine and L-Arginine Derivatives Identified as Activators of Human PMN-Leukocyte 'In Vitro'".
P. Cornaglia Ferraris, "Substituted Purines as Immunomodulators: Speculative Considerations"; EOS n. 2, vol. IV (1984).
p. A-829 from Italian Pharmaceutical Directory.
p. 4853 From the Merck Index, 9th Edition.
Gilman "Organic Chemistry", vol. 2, p. 1079 (1943).

*Primary Examiner*—Nicholas S. Rizzo
*Attorney, Agent, or Firm*—Bucknam and Archer

[57] ABSTRACT

The invention relates to a series of purine derivatives of formula (I)

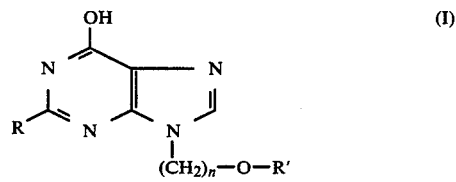

wherein R is hydrogen or NH$_2$, n is an integer from 1 to 6, R$^1$ is one of the following chains:

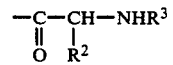

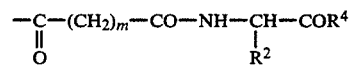

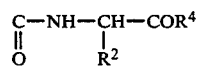

wherein R$^2$ is the residue of an aminoacid, R$^3$ is hydrogen or the residue of an oligopeptide and R$^4$ is OH or the residue of an oligopeptide.

14 Claims, 2 Drawing Figures

COMPOUNDS ENDOWED WITH IMMUNOMODULATING ACTIVITY

This invention relates to a new series of specific immuno-modulator compounds, of the general formula I $$\begin{array}{c} OH \\ | \\ N \diagup \diagdown N \\ R-\diagdown N \diagup \diagdown N \diagup \\ | \\ (CH_2)_n-O-R^1 \end{array} \quad (I)$$

wherein:
R is hydrogen or $NH_2$
n is an integer from 1 to 6;
$R^1$ represents:
a chain of the formula $$-\underset{\underset{O}{\|}}{C}-\underset{\underset{R^2}{|}}{CH}-NHR^3$$

wherein
$R^2$ is the residue of an α-aminoacid and
$R^3$ is hydrogen or the residue of an oligopeptide containing 2 to 6 aminoacids;
a chain of the formula $$-\underset{\underset{O}{\|}}{C}-(CH_2)_m-CO-NH-\underset{\underset{R^2}{|}}{CH}-COR^4$$

wherein
m is an integer from 2 to 6,
$R^2$ has the above mentioned meanings,
$R^4$ is OH or the residue of an oligopeptide containing 2 to 6 aminoacids;
a chain of the formula $$\underset{\underset{O}{\|}}{C}-NH-\underset{\underset{R^2}{|}}{CH}-COR^4$$

wherein
$R^2$ and $R^4$ have the above mentioned meanings;
when n=1, a chain of the formula $$-(CH_2)_p-OCO-\underset{\underset{R^2}{|}}{CH}-NHR^3$$

wherein
p is an integer from 2 to 6, and
$R^2$ and $R^3$ have the above mentioned meanings or a chain of the formula $$-(CH_2)_p-OCO-(CH_2)_m-CO-NH-\underset{\underset{R^2}{|}}{CH}-COR^4$$

wherein
m, p, $R^2$ and $R^4$ have the above mentioned meanings.
According to another object, this invention provides a process for the preparation of purine derivatives of formula I.

Still another object of this invention is to provide pharmaceutical compositions with immuno-modulating activity containing as active principle one or more compounds of formula (I).

According to the invention "immuno-modulating activity" means the ability to interact with immunocompetent cells providing them with activation's messages.

The recent immuno-pharmacological investigations have developed a series of extractive polypeptides, with thymic hormone functions, which are employed in clinical medicine as coadjuvants for the treatment of some infectious diseases, especially viral ones, and of malignant neoplastic forms.

For instance, it is known a drug containing twelve different polypeptides and extracted from calf's thymus. Such a drug aims to stimulate the immunitary control against viruses, bacteria and even neoplastic cells' attacks.

The aminoacidic sequence of the different extracted polypeptides is yet unknown. Moreover, it is not clear their specific action in the regulation of the immunitary functions.

Other immuno-pharmacological studies led to the discovery, among synthetic derivatives of adenosine, Of some principles active on the human immunitary system, giving, as the clinical result, an immune activation against numerous viral -DNA or -RNA strains.

However, also in this case, the activation of the immunitary system is aspecific and it doesn't seem to have selectivity on one or another lymphocytic functions (stimulation or depression of antibodies' response, etc.)

Likely, the activation exercised by those drugs on non-committed lymphocytic functions is casual.

It is therefore the main object of the present invention to provide specific immunomodulating compounds, able to activate only cellular compartments with specific functions.

According to the invention, it has been found that such an object can be attained by the use of compounds of the above formula (I), in which the α-aminoacids may be the same or partially or entirely different.

In the second case, the aminoacids themselves are condensed each other according to pre-established sequences. Preferably the α-aminoacids are in the laevorotatory form, although they can be used also in the dextrorotatory or racemic forms.

Examples of α-aminoacids which can be contained in the compounds of formula (I) are glycine, alanine, valine, leucine, isoleucine, serine, threonine, aspartic acid, glutamic acid, arginine, lysine, cysteine, cystine, methionine, phenylalanine, thyrosine, tryptophan, proline, histidine. As already mentioned, these α-aminoacids are linked by typical peptidic bonds, in which the amino group of one aminoacid is connected with an amidic bond to the carboxyl group of another aminoacid, and so on.

According to the invention, it is indifferent whether the hydroxypyrimidine ring of the purinic nucleus is in enolic form, as shown in the formula (I), or in the tautomeric ketoform, or in an equilibrium mixture of both forms.

The nature and the sequence of the aminoacids linked to the purine ring involve a qualitative change of the hormone-like message, which constitutes the chemico-cellular function of compounds (I).

Therefore, with such compounds, it is possible to activate only those cellular compartments with specific functions. In comparison with analogous compounds already known they allow a clinical use much better definite for pathologies such as immunodeficiencies, disreactive or autoimmune diseases and malignant neoplastic diseases themselves.

As above mentioned, the processes for the preparation of compounds of formula I, are also within the purposes of the invention.

These processes can be briefly summarized in the following schemes, wherein, for the sake of brevity, P represents the hydroxypurinic part of the formula I:

SCHEME A

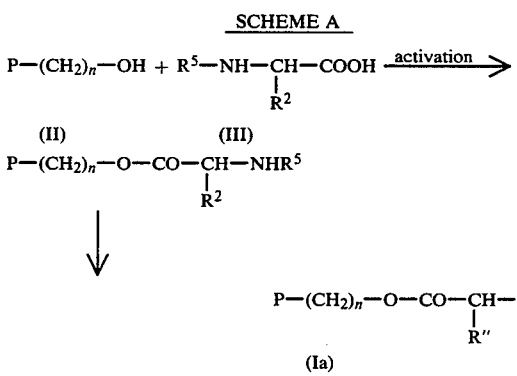

wherein, n, $R^2$ and $R^3$ have the above mentioned meanings, $R^5$ is one of the protective groups usually employed in the peptide synthesis or the residue of an oligopeptide containing 2 to 6 aminocids having the terminal aminogroup protected.

The activation of the carboxy group is performed by any one of the agents which are usually employed for this purpose, such as dicyclohexylcarbodiimide, N,N'-carbonyldi-imidazole, and analogous reagents.

SCHEME B

P—(CH$_2$)$_n$—OH ⟶

(II)

P—(CH$_2$)$_n$—O—C(=O)—(CH$_2$)$_m$—COOH ⟶

(IV)

P—(CH$_2$)$_n$—O—C(=O)—(CH$_2$)$_m$—CO—NH—CH(R$^2$)—COR$^4$ (Ib)

wherein n, m, $R^2$ and $R^4$ have the above mentioned meanings.

The step from (IV) to (Ib) can be carried out through activation of the carboxyl group of IV, in an way per se known, and reaction with an aminoacid or a peptide in which again the carboxyl group is protected if desired.

SCHEME C

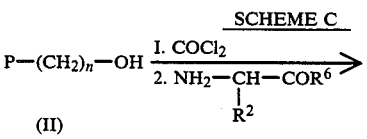

-continued
SCHEME C

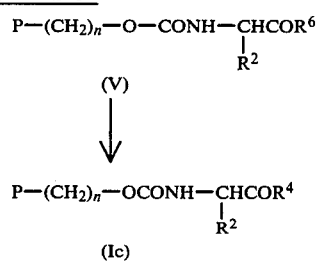

wherein m, $R^2$ and $R^3$ have the above meanings and $R^6$ is a protective group for the carboxyl group or the residue of an oligopeptide containing 2 to 6 aminoacids having the terminal carboxyl group protected. The step from (V) to (Ic) can be readily accomplished by simple cleavage of the protective group.

According to similar schemes, compounds I, with side chains different than those which have been previously illustrated, can be prepared.

Moreover, the compounds according to the invention or the corresponding intermediates can be prepared from similar compounds having, instead of the hydroxy group on the pyrimidine ring, a chlorine atom, which can be transformed into the hydroxy group by a nucleophilic displacement reaction which is per se known.

The starting materials (II), of the formula P—(CH$_2$)$_n$—OH, wherein n is an integer from 1 to 6, can be prepared as described by Schaeffer H. S. et al.; J. Med. Chem. 1968, p. 21, according to the following scheme:

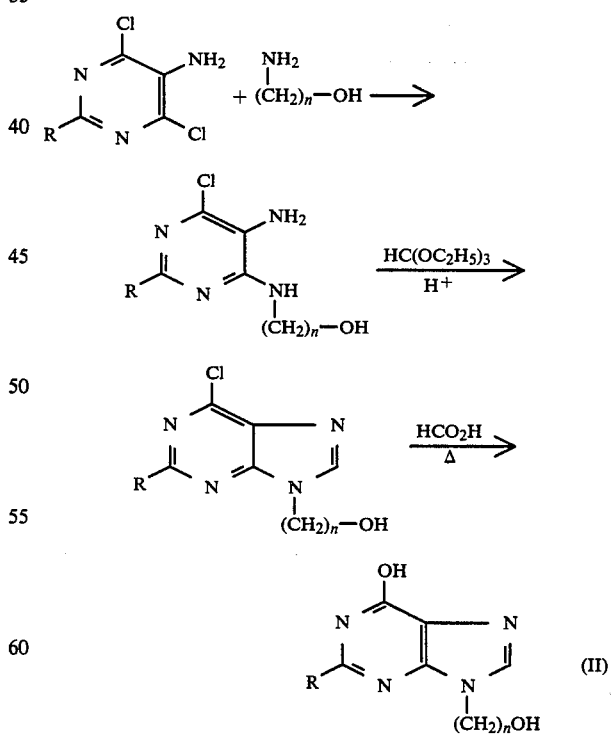

In table I, there are reported melting points and elemental analysis data for the intermediates, wherein n is 2 to 6, and of the corresponding hemisuccinates(IV), prepared by reaction with succinic anhydride in pyridine. Both in the table and in the following examples, P' represents the residue

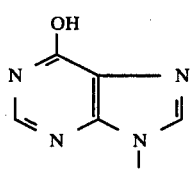

TABLE I

| Compound No | n | m.p. | C calcd % | C found % | H calcd % | H found % | N calcd % | N found % |
|---|---|---|---|---|---|---|---|---|
| P'—(CH$_2$)$_n$OH (II) | | | | | | | | |
| (II,2) | 2 | 277* | 46.66 | 46.54 | 4.47 | 4.63 | 31.09 | 30.87 |
| (II,3) | 3 | 251 | 49.48 | 49.52 | 5.19 | 5.22 | 28.85 | 29.01 |
| (II,4) | 4 | 200 | 51.91 | 51.88 | 5.81 | 5.90 | 26.91 | 26.70 |
| (II,5) | 5 | 237 | 54.04 | 53.96 | 6.35 | 6.51 | 25.21 | 25.50 |
| (II,6) | 6 | 225 | 55.92 | 55.60 | 6.82 | 7.00 | 23.71 | 24.03 |
| P'—(CH$_2$)$_n$OCO(CH$_2$)$_2$CO$_2$H (IV) | | | | | | | | |
| (IV,2) | 2 | 214–216 | 47.15 | 46.84 | 4.31 | 4.22 | 19.99 | 20.34 |
| (IV,3) | 3 | 170–172 | 48.98 | 48.59 | 4.79 | 4.67 | 19.04 | 18.95 |
| (IV,4) | 4 | 145–147 | 50.65 | 50.43 | 5.23 | 5.11 | 18.17 | 17.86 |
| (IV,5) | 5 | 136–138 | 52.17 | 52.30 | 5.63 | 5.90 | 17.38 | 17.47 |
| (IV,6) | 6 | 121–123 | 53.56 | 53.59 | 5.99 | 6.09 | 16.66 | 16.15 |

*m.p. = 262, Kondo et al., Makromol. Chem. 1969, 298–301

The following examples further illustrate the invention, without limiting it, with reference both to single compounds and to the preparation processes.

EXAMPLE 1

9-(2-Hydroxyethyl)-6-hydroxy-purine hemisuccinate (IV, 2)

$$P-(CH_2)_2-OCO-CH_2-CH_2-CO_2H \quad\quad (IV, 2)$$

Method A 1.24 g of succinic anhydride (12.3 mmoles) are dissolved in 20 ml of hot pyridine; then 0.740 g of 9-(2-hydroxyethyl)-6-hydroxy-purine (4.1 mmoles) and a tip of spatula of DMAP (dimethylaminopyrimidine) is added. The mixture is refluxed under stirring for 22 hours. Then the pyridine is evaporated and the residue is washed twice with ethanol to eliminate the excess succinic acid.

After filtration, the residue is oven dried. M.p. 210°–215° C. The compound is unitary in TLC (EtOH 80%—triethylamine 20%). The structure of the compound is confirmed by the IR spectrum.

Method B 0.200 g (1 mmole) of 9-(2-hydroxyethyl)-6-chloropurine are treated with 1 g of succinic anhydride in conditions similar to those described in the previous example.

The pyridine is evaporated and the residue is dissolved in 10 ml of formic acid; the mixture is refluxed for 30 minutes. After cooling, 20 ml of methanol are added and the precipitate is filtered with suction. 205 mg of hemisuccinate (IV, 2) are thus obtained.

EXAMPLE 2

6-Hydroxy-9-(2-(2-chlorocarbonyl-ethyl)-carbonyloxy-ethyl)-purine hydrochloride $$P'-(CH_2)_2-OCO-CH_2-CH_2-COCl$$

HCl 100 mg of hemisuccinate (IV, 2) are dissolved in 5 ml of SOCl$_2$ at room temperature. The reaction mixture is stirred for 24 hours at room temperature. The excess, thionyl chloride is evaporated under reduced pressure (water pump), the white solid residue is dissolved in anhydrous ethyl ether filtered with suction and washed with ethyl ether many times. There are obtained quantitative yields of 6-hydroxy-9-(2-(2-chlorocarbonyl-ethyl)-carbonyloxy-ethyl)-purine hydrochloride, as a white microcrystalline solid with decomposition point >200° C.

The structure of the compound was determined by transformation into its methyl ester, m.p. 183°–185° C., which has been identified by NMR and mass spectra.

EXAMPLE 3

6-Hydroxy-9-{2-[2-amino-3-(4-hydroxyphenyl)propionyloxy]}-ethyl-purine (Ia, 1)

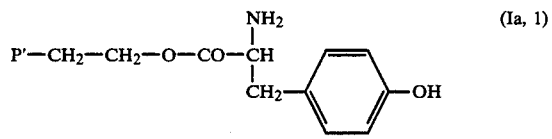

Method A 371 g (1 mmole) of O-benzyl-N-Boc-thyrosine are dissolved in anhydrous DMSO and treated with 368 mg (2 mmoles) of carbonyldiimidazole. The reaction mixture is heated to 70° C. for 5 hours and then added to a solution of 9-(2-hydroxyethyl)-6-hydroxypurine (280 mg, 1 mmole) in 5 ml of pre-heated (70° C.) dimethylsulfoxyde, containing 20 mg of 4-dimethylamino-pyridine. The reaction mixture is kept at 70°–80° C. for about 2 hours, then it is cooled and treated with water (50 ml). The separated oil is extracted with ethyl acetate (2×25 ml), the pooled extracts are dried and freed from the solvent by evaporation under reduced pressure. The oily residue, without further purification, is dissolved in 20 ml of ethanol, treated with 5 ml of cyclohexene and 120 mg of palladium-charcoal at 10% and refluxed under stirring for 2 hours. During this time a precipitate is formed, which is dissolved in acetic acid.

The charcoal is filtered off, 4–5 drops of trifluoroacetic acid are added and the mixture is refluxed for 30 minutes. The solvent is evaporated under vacuum and the residue is washed with methanol. Compound (Ia,1) is obtained in a 87% yield.

Colourless crystals with m.p. 235°–240° C.

NMR in DMSO (δ from TMS): 3.0 2H (doublet) CH$_2$—CH, 4.0 1H (triplet) CH—CH$_2$, 4.10 4H (singlet) CH$_2$—CH$_2$, 6.6–7.0 4H (AA', BB') C$_6$H$_4$, 7.9 and 8.0 2H (singlets) purine hydrogens, 11.0 4H (broad band) exchangeable hydrogens.

Method B

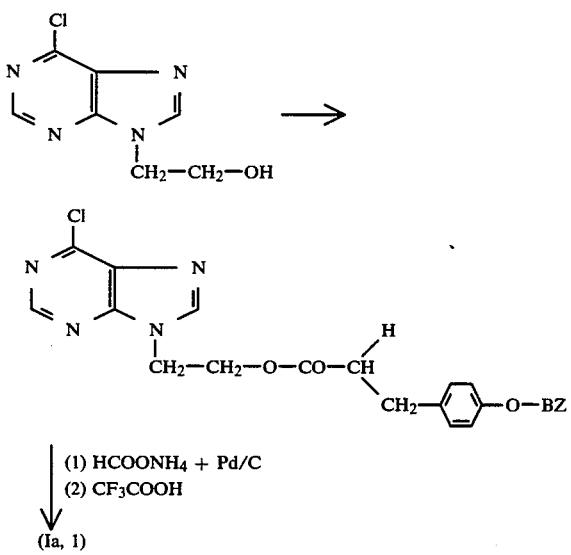

(1) HCOONH₄ + Pd/C
(2) CF₃COOH (Ia, 1)

371 mg (1 mole) of O-benzyl-N-Boc-thyrosine are dissolved in anhydrous acetonitrile (20 ml). To the solution 198 mg of 9-(2-hydroxyethyl)-6-chloro-purine, 210 mg of dicyclohexylcarbodiimide and 25 mg of 4-pyrrolidino-pyridine are added. After heating at 60° C. for 12 hours, the reaction mixture is cooled, the dicyclohexylurea is filtered off and the solvent is eliminated from the filtrate by distillation under reduced pressure. The residue, without further purification, is dissolved in a 50/50 mixture of methanol/acetic acid. To the so obtained solution 100 mg of palladium/charcoal and 500 mg of ammonium formiate are added. After stirring at room temperature for 30 minutes, the catalyst is filtered off and the solvent is removed from the filtrate by evaporation under reduced pressure.

The residue is treated with 50% trifluoroacetic acid containing 10% anisole for about 1 hour.

Methanol (15 ml.) is added, the temperature is kept at 5° C. for 24 hours. The precipitate produced is filtered, which is identical to the product described in Example 4, method A.

EXAMPLE 4

6-Hydroxy-9-{2-[2-(carboxymethylaminocarbonyl)ethyl]-carbonyloxy ethyl}purine (Ib, 1)

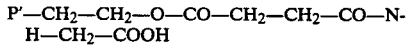

(A) 2.8 g (10 mmoles) of 9-(2-hydroxyethyl)-6-hydroxy-purine hemisuccinate prepared in Example 1, are transformed in the chloride hydrochloride as described in Example 2. The so-obtained amorphous powder is suspended in 20 ml of anhydrous CH₂Cl₂ and treated with 4.95 g (30 mmoles) of glycine benzyl ester in 30 ml of CH₂Cl₂. The reaction mixture is stirred at room temperature for 3 hours, then filtered. The filtrate, washed with 30 ml of saturated NaHCO₃ solution and with 30 ml of saturated NaCl solution, is dried on Na₂SO₄ and evaporated under reduced pressure.

The residue is purified by column chromatography on silica gel using ethyl acetate/methanol (1:1) as eluent.

After crystallization from ethanol, 2.3 g (52% yield) of 6-hydroxy-9-{2-[2-(benzyloxy)carbonylmethylaminocarbonyl)ethyl]carbonyloxy}ethyl purine, as a white crystalline powder melting at 158°-160° C., are obtained.

Elemental analysis: $C_{20}H_{21}N_5O_6$

|   | Found | Calculated |
|---|---|---|
| C | 56.31% | 56.20% |
| H | 4.73% | 4.91% |
| N | 15.98% | 16.39% |

NMR (CDCl₃+DMSO-d⁶; δ TMS) 2.65 δ 4H (singlet) CO—CH₂—CH₂—CO, 3.95 δ 2H (singlet) NH—CH₂—CO 4.40 δ 4H (broad singlet) N—CH₂—CH₂—O, 5.23 δ 2H (singlet) CH₂—C₆H₅, 7.26 δ 5H (singlet) C₆H₅, 7.95 and 8.10 δ 2H (singlets) purine hydrogens, 10 δ 2H (broad band) NH and OH.

(B) 220 mg (0.5 mmoles) of the compound prepared in (A), are dissolved in methanol and treated, under stirring, with 86 mg (1.6 mmoles) of ammonium formiate and 100 mg of palladium on charcoal (10%).

The mixture is stirred for 1 hr at 40° C., 40 mg of ammonium formiate are then added and stirring is continued for 1 hour more. When the end of the debenzylation reaction is evidenced by TLC (ethyl acetate/methanol 1:1), the reaction mixture is filtered on celite and the filtrate is evaporated. The crude product is treated with ethanol, filtered and the precipitate is crystallized from methanol/water (90:10).

97 mg (55% yield) of white crystalline (Ib-1), melting at 186°-190° C. with decomposition, are obtained.

Elemental analysis: $C_{13}H_{15}N_5O_6$

|   | Found | Calculated |
|---|---|---|
| C | 46.39% | 46.29% |
| H | 4.25% | 4.45% |
| N | 20.97% | 20.75%. |

NMR (CD₃OD+TFA), δ TMS:

2.63 δ 4H (singlet) CO—CH₂—CH₂—CO, 3.98 δ 2H (singlet) NH—CH₂—CO, 4.65 δ 4H (multiplet) N—CH₂—CH₂—O, 8.2 and 9.25 δ 2H (singlets) purine hydrogens.

EXAMPLE 5

6-Hydroxy-9-{2-[2-(1-carboxy)ethylaminocarbonylethyl]carbonyloxy ethyl}purine (Ib-2)

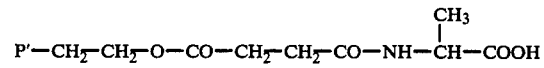

(A) 2.8 g (10 mmoles) of 9-(2-hydroxyethyl)-6-hydroxy-purine hemisuccinate (IV-2) are transformed into the chloride hydrochloride and treated with 5.2 g (30 mmoles) of DL-alanine benzyl ester dissolved in 30 ml of CH₂Cl₂.

The reaction mixture is stirred at room temperature for 6 hours and then worked up as described in Example 4A. 2.6 g (57%) of 6-hydroxy-9-{2-[2-(1-benzyloxycarbonylethylaminocarbonyl)ethyl]carbonyloxy}ethyl purine are obtained by crystallization from water as white crystals melting at 140°-142° C.

Elemental analysis: $C_{21}H_{23}N_5O_6$

|   | Found | Calculated |
|---|---|---|
| C | 57.01% | 57.14% |

|   | Found | Calculated |
|---|-------|------------|
| H | 5.01% | 5.21% |
| N | 15.69% | 15.87%. |

NMR (CDCl$_3$+DMSO; δ TMS): 1.45 δ 3H (doublet) C$\underline{H}_3$—CH, 2.65 δ 4H (singlet) CO—CH$_2$—CH$_2$—CO, 4.45 δ 1H (quarter) C$\underline{H}$—CH$_3$, 4.58 δ 4H (broad singlet) N—CH$_2$—CH$_2$—O, 5.23 δ 2H (singlet) C$\underline{H}_2$—C$_6$H$_5$, 7.25 δ 5H (singlet) C$_6$H$_5$, 7.95 and 8.08 δ $\overline{2H}$ (singlets) purine hydrogens, 10–11 δ 2H (broad signal) NH and OH.

(B) 226 mg (0.5 mmoles) of the compound obtained as described in (A) are dissolved in methanol (20 ml) and debenzylated as in Example 4B. After crystallization from ethanol there are obtained, 103 mg (57%) of (Ib-2) as a white crystalline solid melting at 172°–178° C.

Elemental analysis: C$_{14}$H$_{17}$N$_5$O$_6$

|   | Found | Calculated |
|---|-------|------------|
| C | 48.18% | 47.86% |
| H | 4.70% | 4.88% |
| N | 21.60% | 21.30%. |

NMR (CD$_3$OD+TFA; δ TMS): 1.45 δ 3H (doublet) C$\underline{H}_3$—CH, 2.60 δ 4H (singlet) CO—CH$_2$—CH$_2$—CO, 4.40 δ 1H (quarter) C$\underline{H}$—CH$_3$, 4.65 δ 4H (broad singlet) N—CH$_2$—CH$_2$—O, 8.10 δ 2H (singlets) purine hydrogens.

EXAMPLE 6

N$^\alpha$-{3-[2-(6-hydroxypurinyl-9)-ethoxy-carbonyl]propionyl}lysine (Ib-3)

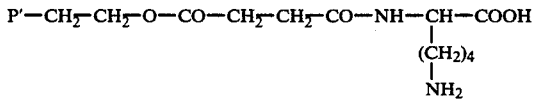

(A) 3.70 g (10 mmoles) of N$^\epsilon$-carbobenzyloxy-L-lysine benzylester and 0.25 ml of triethylamine are dissolved in anhydrous methylene chloride (50 ml) and added to a suspension in CH$_2$Cl$_2$ of the chloride hydrochloride obtained from 2.8 g (10 mmoles) of hydroxyethyl derivative (IV-2). The reaction mixture is stirred for 4 hours at room temperature, then filtered. The filtrate is evaporated under reduced pressure and the residue is treated with ethanol to give a white precipitate which is crystallized from ethanol/water (90:10) yielding 3.28 g (52%) of N$^\epsilon$-carbobenzyloxy-N$^\alpha$-{3-[2-(6-hydroxypurinyl-9)ethoxy-carbonyl]propionyl}lysine benzyl ester, melting at 134°–136° C.

Elemental analysis: C$_{32}$H$_{36}$N$_6$O$_8$

|   | Found | Calculated |
|---|-------|------------|
| C | 60.35% | 60.75% |
| H | 5.73% | 5.69% |
| N | 13.20% | 13.29%. |

NMR (CDCl$_3$+DMSO; δ TMS): 1–1.6 δ 6H (multiplet) CH$_2$—CH$_2$—C$_2$, 2.6 δ 4H (singlet) CO—CH$_2$—CH$_2$—CO, 3.1 δ 2H (triplet) C$\underline{H}_2$—NH, 4.4 δ 5H (broad singlet) N—CH$_2$—CH$_2$—O+—CH—COOBz, 5.03 and 5.13 δ 4H (double singlet) C$\underline{H}_2$—C$_6$H$_5$, 7.3 δ 10H (singlet) C$_6$H$_5$, 7.95 δ 2H (singlet) purine hydrogens, 9–11 δ 3H (broad signal) NH, OH.

(B) 632 mg of the preceding compound are debenzylated according to the method described in Example 4B.

403 mg of crude (IB-3) are obtained, which were crystallized from water to give 345 mg (76%) of pure (Ib-3) as a white, hygroscopic powder. M.p. undefined.

NMR (DMSO+D$_2$O; δ TMS): 1.8 6H (multiplet) CH$_2$—CH$_2$—CH$_2$, 2.6 4H (multiplet) CO—CH$_2$—CH$_2$—CO, 3.2 2H (triplet) C$\underline{H}_2$—NH$_2$, 3.6 1H (triplet) C$\underline{H}$—CH$_2$, 4.45 δ 4H (singlet) O—CH$_2$—CH$_2$—N, 8.05 δ 2H (singlet) purine hydrogens.

EXAMPLE 7

N-{3-[2-(6-hydroxypurinyl-9)-ethoxycarbonyl]propionyl}-N'-(4-carboxy-4-amino-butyl)guanidine (1b-4)

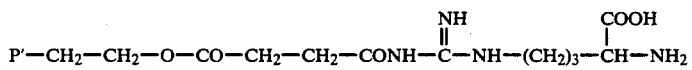

The chloride hydrochloride obtained from 300 mg (1.07 mmoles) of (IV, 2) is suspended in 5 ml of anhydrous dimethylformamide. To this suspension, under stirring, 330 mg of N$_\alpha$-Z-L-arginine (mmoles 1.07) and 0.2 ml of triethylamine dissolved in 4 ml of dimethylformamide are added. The reaction mixture is stirred for three hours, the solvent is then removed and the crude product is purified by gel filtration. The eluate is lyophilized and the product is dissolved in 30 ml of methanol. To the solution, 100 mg of ammonium formiate and 50 mg of palladium/charcoal are added; after three hours at 40°–45° C., under stirring, the reaction mixture is filtered on celite, the solvent is saturated with HCl. The precipitate is filtered, washed with isopropanol and dried under vacuum with P$_2$O$_5$. 195 mg of (Ib-4) as a white, amorphous and hygroscopic product, melting with decomposition at >200° C. (sealed tube).

NMR (DMSO+D$_2$O); δ TMS: 1.78 δ 4H (multiplet) —CH$_2$—CH$_2$—, 2.55 δ 4H (singlet) CO—CH$_2$—CH$_2$—CO, 3.35 δ 2H (triplet) C$\underline{H}_2$—NH—, 3.55 δ 1H (triplet) C$\underline{H}$—CH$_2$, 4.40 δ 4H (singlet) N—CH$_2$—CH$_2$—O, 8.03 and 8.06 δ2H (singlet) purine hydrogens.

EXAMPLE 8

N$^\alpha$-{3-[2-(6-hydroxypurinyl-9)ethoxy-carbonyl]propionyl}-tyrosine (Ib-5)

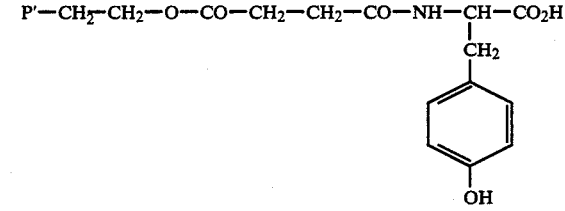

181 mg (1 mmole) of L-thyrosine are added to a solution of 400 mg of sodium hydrogencarbonate in 10 ml of deionized water. To the so obtained solution 340 mg of chloride hydrochloride of example 2 are added, keeping the reaction temperature below 10° C.

When the reaction is completed (30′) the pH is adjusted to 7 with 5% HCl, and the solution is freeze-dried. The lyophilizate is treated with anhydrous hot methanol, and the so obtained solution is cooled and centrifugated. The supernatant, after evaporation of the solvent under vacuum gives a white microcrystalline product, which shows analytical and spectroscopical features corresponding to compound (Ib-5).

NMR (DMSO; δ TMS): 2.5 δ 4H (singlet) CO—CH$_2$—CH$_2$—CO, 3.05 δ 2H (doublet) CH$_2$—CH, 3.98 δ 1H (multiplet) CH—CH$_2$, 4.45 δ H (singlet) N—CH$_2$—CH$_2$—O, 6.6–7.0 δ 4H (AA′BB′) —C$_6$H$_4$—, 7.9 and 8.0 δ 2H (singlets) purine hydrogens, 9 δ 1H (doublet) NH, 11.5 δ 2H (broad band) OH.

EXAMPLE 9

6-Hydroxy-9-{6-[2-(carboxyethyl)aminocarbamoyloxy]hexyl}purine (Ic-1)

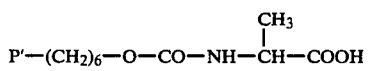

(A) To 2.2 g (9 mmoles) of 9-(6-hydroxyhexyl)ipoxantine (II, 6), suspended in 50 ml of anhydrous toluene are added, under stirring, 5 ml of a 20% solution of phosgene in toluene. The reaction mixture is stirred for 3 hours at room temperature, a flow of anhydrous nitrogen is let in to remove the excess phosgene and 5.2 g (30 mmoles) of DL-alanine benzyl ester, dissolved in 30 ml of CH$_2$Cl$_2$, are added. After 1 hour stirring the precipitate is filtered and the filtrate is evaporated under reduced pressure. The residue is treated with ethanol, filtered and crystallized from water to give a white crystalline powder in a 7% yield (m.p. 167°–168° C.).

Elemental analysis: C$_{22}$H$_{27}$N$_5$O$_5$

| | Found | Calculated |
|---|---|---|
| C | 59.60% | 59.86% |
| H | 6.02% | 6.12% |
| N | 15.63% | 15.87% |

NMR (DMS; δ TMS): 1.35 δ 8H (singlet) C—(CH$_2$)$_4$—C, 1.48 δ 3H (doublet) CH$_3$—CH, 4.0 δ 4H (2 triplets) CH$_2$—O and CH$_2$—N, 4.43 δ 1H (quartet) CH—CH$_3$, 5.23 δ 2H (singlet) CH$_2$—C$_6$H$_5$, 7.3 δ 5H (singlet) C$_6$H$_5$, 7.80 and 8.30 δ 2H (2 singlets) purine hydrogens, 9–11 δ 2H (broad signal) OH, NH.

(B) 440 mg (1 mmole) of the preceding compound are debenzylated according to the method described in the Example 4B. 318 mg (90%) of the acylalanine derivative (Ic-1) are obtained as a white powder (m.p. >220° C.).

Elemental analysis: C$_{15}$H$_{21}$N$_5$O$_5$

| | Found | Calculated |
|---|---|---|
| C | 51.00% | 51.28% |
| H | 6.02% | 5.98% |
| N | 20.31% | 19.94% |

NMR (DMSO+D$_2$O; δ TMS): 1.33 δ 8H (broad singlet) C—(CH$_2$)$_4$—C, 1.45 δ 3H (doublet) CH$_3$—CH, 3.94 δ 2H (triplet) CH$_2$—N, 4.12 δ 2H (triplet) CH$_2$—O, 4.40 δ 1H (quartet) CH—CH$_3$, 7.95 and 8.12 2H (2 singlets) purine hydrogens.

EXAMPLE 10

6-Hydroxy-9-{5-[2-(carboxyethyl)amino-carbamoiloxy]pentyl}purine (Ic-2)

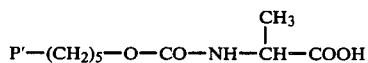

(A) According to the same method described in the Example 9, starting from 9-(5-hydroxypentyl)hypoxantine (II-5), 6-hydroxy-9-{5-[2-(benzyloxycarbonyl-ethylamino-carbamoyl)oxy]pentyl}purine (m.p. 184° C.).

Elemental analysis: C$_{21}$H$_{25}$N$_5$O$_5$

| | Found | Calculated |
|---|---|---|
| C | 57.31% | 57.66% |
| H | 5.62% | 5.72% |
| N | 16.20% | 16.01% |

NMR (DMSO; δ TMS): 1.36 δ 6H (broad singlet) C—(CH$_2$)$_3$—C, 145 δ 3H (doublet) CH$_3$—CH, 4.03 δ 4H (two triplets) CH$_2$—O and CH$_2$N, 4.43 δ 1H (quartet) CH—CH$_3$, 5.23 δ 2H (singlet) CH$_2$—C$_6$H$_5$, 7.3 δ 5H (singlet) C$_6$H$_5$, 7.80 and 8.28 δ2H (singlet) purine hydrogens, 9–11 δ 2H (broad signal) OH, NH.

(B) Starting from the preceding compound, following the same procedure of the Example 9B, (Ic-2) has been obtained (m.p. 200° C., decomposition).

Elemental analysis: C$_{14}$H$_{19}$N$_5$O$_5$

| | Found | Calculated |
|---|---|---|
| C | 49.80% | 49.85% |
| H | 5.82% | 5.63% |
| N | 20.45% | 20.87% |

NMR (DMSO+D$_2$O: δ TMS): 1.35 δ 6H (broad singlet) C—(CH$_2$)$_3$—C, 1.45 δ 3H (doublet) CH$_3$—CH, 3.95 δ 2H (triplet) CH$_2$—N, 4.12 δ 2H (triplet) CH$_2$—O, 4.40 1H (quartet) CH—CH$_3$, 7.95 and 8.10 δ 2H (singlets) purine hydrogens.

The compounds of this invention have been shown to possess a specific immunomodulator activity which is superior to that of the control dougs, such as methisoprinol, already widely employed in clinical medicine.

In FIG. 1, the effects of compound (Ib-4) are shown in comparison with methisoprinol on the stimulation by phytohemagglutinin (PHA) of lymphocytes extracted by patients affected by Hodgkin's disease and off-therapy since, at least, 17 months. The PHA response of lymphocytes of these patients are below normal range.

The in vitro effect of (Ib, 4) and methisoprinol on the stimulation by PHA of lymphocytes was studied by cultivating PHA stimulated lymphocytes in the presence of these compounds at different doses: methisoprinol at 100, 200, 400 γ/ml; (Ib-4) at 0.1, 0.5, 1 and 5 γ/ml.

The plot of FIG. 1 is representative of the general trend found on lymphocytes extracted by several patients: compound (Ib-4) produces a marked enhancement of the PHA response, already at a dose of 0.1 γ/ml, while methisoprinol needs a higher dosage (200–400 γ/ml) to induce a stimulating effect which is less than that produced by (Ib-4).

Moreover it is important to consider that concentrations of 0.1-1 γ/ml are physiologic and easily achieved in vivo; on the contrary it is difficult to achieve in vivo concentrations as high as those needed by methisoprinol for its maximum effects.

The experimental results are therefore indicative of a more effective therapeutic use of the compounds of this invention in comparison with methisoprinol.

Figure 2:
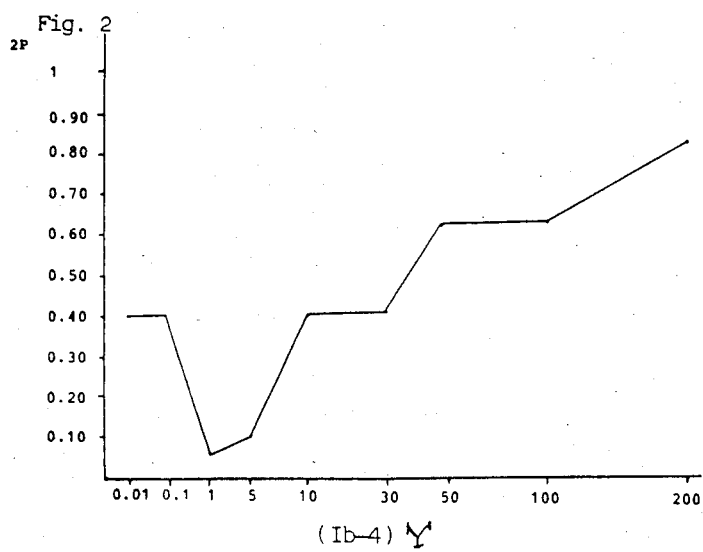

In FIG. 2 the results of the study of the effect of (Ib-4) on the polymorphonuclear (PMN) lymphocytes membrane-stimulated oxidative metabolic activity are reported: polymorphonuclear leucocytes ($2.5 \times 10^4$/ml) in phosphate buffer solution (PBS) were incubated for 15' at 37° C. with ferricytochrome C (1.5 mg/ml) in the presence or absence of superoxide dismutase (SOD) (0.125 mg/ml) after the addition of 50 μl of stimulating agent.

The amount of reduced cytochrome C in che cell free supernatant was determined spectrophotometrically at 550 nm and the $O_2^-$ release calculated according to a standard formula. Appropriate control tubes contained fixed doses of (Ib-4) (from 0.01 γ/ml to 200 γ/ml). From the results, statistically evaluated by a T-test for paired data, it is evident a statistically significant enhancement in the superoxide production at a dose of 1 γ/ml of (Ib-4). At higher dosages, probably because of complex mechanisms of metabolic regulation, there is a gradual decrease of the $O_2^-$ production. An enhanced production of superoxide anion is indicative of a more effective phagocytic activity.

Ib-4 is also active, at doses ranging from 0.001 to 40 μg/ml, in inhibiting the incorporation of labelled thymidine stimulated by phytohemagglutinin (PHA) or lypopolysaccharides (LPS), in spleen cells from BALB/C mice 8-10 weeks old. The inhibition of the proliferation in vitro is dose-dependent and it is probably due to activation of suppressor cell mechanism. In the following table the results of thymidine incorporation in a $10^6$ cells/ml culture have been listed.

TABLE

| Mitogens | Drug | Thymid. inc. |
|---|---|---|
| Q | 0 | 731+/−86 |
| PHA | 0 | 3089+/−177 |
| LPS | 0 | 15631+/−215 |
| PHA | 40 μg/ml | 159+/−13 |
| LPS | " | 329+/−23 |
| PHA | 20 μg/ml | 241+/−16 |
| LPS | " | 385+/−38 |
| PHA | 15 μg/ml | 141+/−40 |
| LPS | " | 405+/−51 |
| PHA | 10 μg/ml | 146+/−19 |
| LPS | " | 385+/−38 |
| PHA | 5 μg/ml | 193+/−50 |
| LPS | " | 445+/−44 |
| PHA | 2.5 μg/ml | 250+/−34 |
| LPS | " | 627+/−40 |
| PHA | 1 μg/ml | 316+/−78 |
| LPS | " | 665+/−19 |
| PHA | 0.1 μg/ml | 721+/−77 |
| LPSD | " | 729+/−51 |
| PHA | 0.01 μg/ml | 850+/−61 |
| LPS | " | 435+/−113 |
| PHA | 0.001 μg/ml | 840+/−87 |
| LPS | " | 4600+/−85 |

The effect of (Ib-4) on the suppressor cell has also been studied using lymphocytes from healthy volunteers, incubated for 48 hours with different drug concentrations then washed and incubated either with autologous lymphocytes stimulated by concanavalin A for 3 days or with allogeneic mitomycin-treated lymphocytes for 5 days (Mixed Lymphocytes Reaction): (Ib-4), at concentrations between 0.1 and 1.5 μg/ml, gave an inhibition of the proliferative response of about 60% in comparison with controls.

The effect of the compounds object of this invention on the ability of T-lymphocytes to form "active" E-rosettes, has also been studied (Pasino e coll., Boll. Ist. Sieroter, Mil. 60, 4, 297-301, 1981).

Lymphocytes were incubated at 4° for 24 hours, then isolated and incubated for 90 min. in the presence or absence of different concentrations of the drug prior to the assay. Data were expressed as % of cells forming rosettes: as an example, compound (Ib-2) gave an enhancement of the percentage from 35 to 50%, at concentrations from 1 and 3 μg/ml; higher concentrations, the percentage of active E-rosettes decreased.

The compounds of the invention proved at last to be active in vivo (mice C 57 Be/6) in enhancing the anti sheeps red blood cells and anti-TNF (Trinitrophenyl)-LPS (lypopolysaccharides), responses, at dosages ranging from 0.1 to 5 mg/kg. On the basis of the Trypan-blue exclusion test, the compounds of the invention proved to be non-cytotoxic even at very high concentrations (60-120 μg/ml), in a human mononuclear peripheral blood cells culture, with a cell viability greater than 98%.

I claim:

1. A compound of formula I

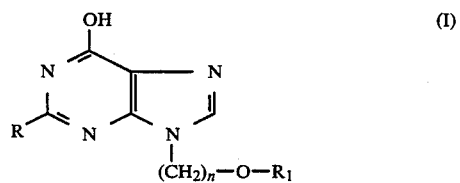

wherein:
R is hydrogen or $NH_2$;
n is an integer from 1 to 6;
$R_1$ is a chain of formula

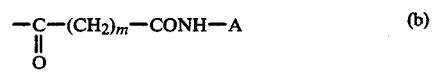

when n = 1, a chain of formula (d)

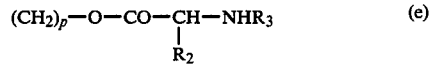

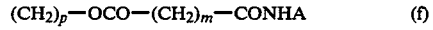

wherein
$R_2$ is the radical attached to the α-carbon atom of an α-aminoacid of formula

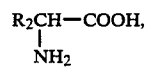

said aminoacid being glycine, alanine, valine, leucine, isoleucine, serine, threonine, aspartic acid, glutamic acid, arginine, lysine, cysteine, cystine, methionine, phenylalanine, tyrosine, tryptophan, proline or histidine;

$R_3$ is hydrogen; p1 m and p are integers ranging independently from 2 to 6,

A is a group of formula

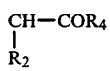

wherein
$R_2$ is as indicated hereinabove,
$R_4$ is OH or
A is a group of formula

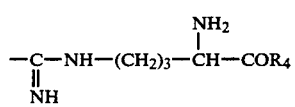

wherein
$R_4$ is as indicated hereinabove.

2. Compounds of claim 1, in which each α-amino acid is in laevorotatory, dextrorotatory or racemic form.

3. Compounds of claim 1, in which each amino acid is a natural amino acid.

4. A pharmaceutical composition with immunomodulator activity, which comprises one or more compounds of formula (I), according to claim 1 and at least one inert carrier.

5. A compound of formula IX

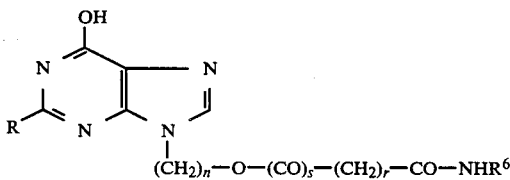

wherein:
n is an integer number between 2 and 6;
r is between 0 and 2;
s is 1;
$R^6$ is a member selected from the group consisting of

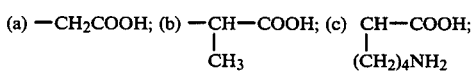

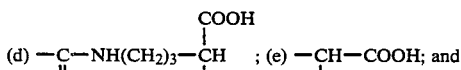

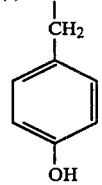

R is H.

6. A pharmaceutical composition with immunomodulator activity, according to claim 4 wherein said compound has formula IX

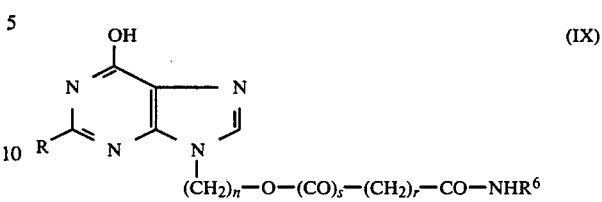

wherein:
n is an integer number between 2 and 6;
r is between 0 and 2;
s is 1;
$R^6$ is a member selected from the group consisting of

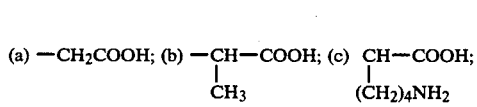

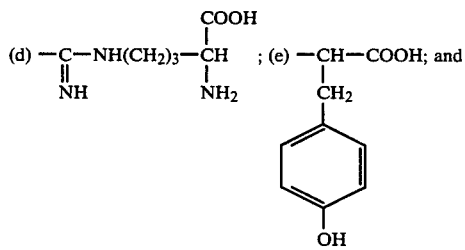

R is H.

7. The compound according to claim 1 of formula

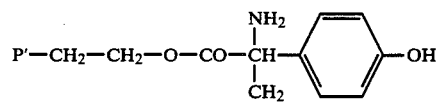

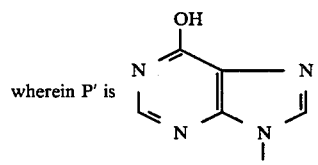

8. A compound according to claim 5 of formula
P'—CH₂—CH₂—O—CO—CH₂—CH₂—CO—NH—CH₂—COOH, wherein P' is

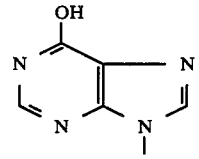

9. The compound according to claim 5 of formula

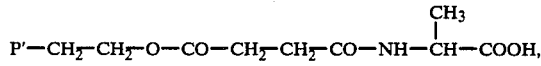

-continued
wherein P' is 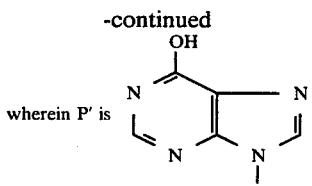
10. The compound according to claim 5 of formula
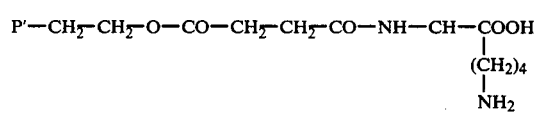
wherein P' is 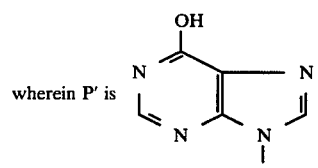
11. The compound according to claim 5 of formula
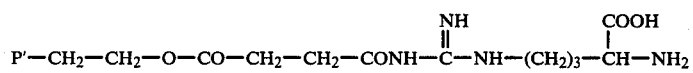
wherein P' is 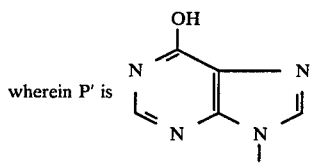
12. The compound according to claim 5 of formula
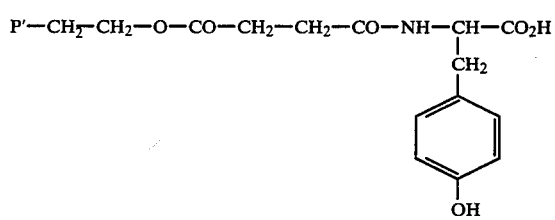
-continued
wherein P' is 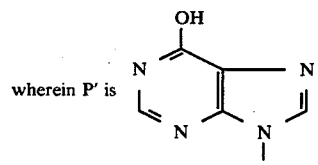
13. The compound according to claim 5 of formula
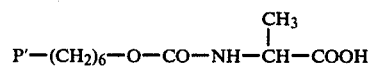
wherein P' is 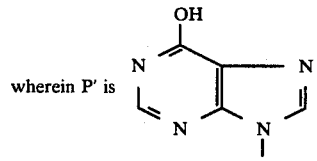
14. The compound according to claim 5 of formula
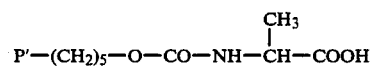
wherein P' is 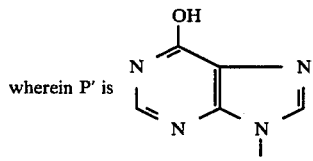
* * * * *